Figure 1:
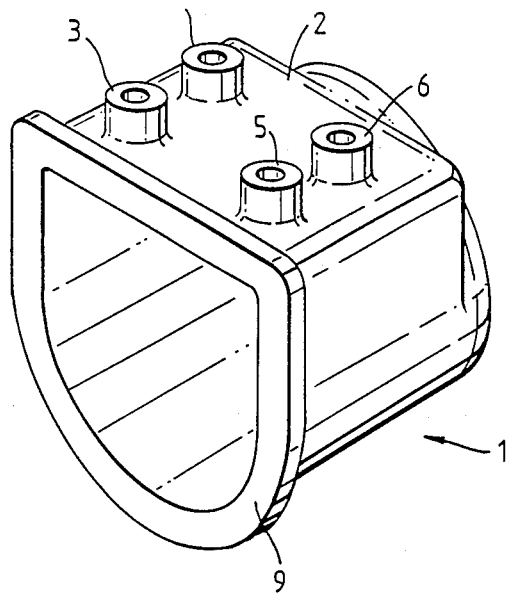

United States Patent [19]

Stepien

[11] Patent Number: 4,854,952
[45] Date of Patent: Aug. 8, 1989

[54] CHROMATOGRAPHY APPARATUS

[75] Inventor: Andrew T. Stepien, Cambridge, England

[73] Assignee: U.S. Philips Corporation, New York, N.Y.

[21] Appl. No.: 228,085

[22] Filed: Aug. 3, 1988

[30] Foreign Application Priority Data

Sep. 2, 1987 [GB] United Kingdom ............... 8720611

[51] Int. Cl.[4] ............................................ B01D 15/08
[52] U.S. Cl. ......................................... 55/386; 55/269;
73/23.1; 106/84; 126/273 R; 210/198.2;
432/248; 501/95
[58] Field of Search ................... 55/67, 197, 208, 269,
55/386; 73/23.1; 126/273 R; 106/84;
210/198.2, 656; 432/248; 501/95

[56] References Cited

U.S. PATENT DOCUMENTS 3,422,603 1/1969 Redmond ............................. 55/386
4,038,055 7/1977 Varano ................................ 55/197
4,420,679 12/1983 Howe .............................. 73/234 X
4,630,594 12/1986 Ellersick .......................... 501/95 X Primary Examiner—Charles Hart
Attorney, Agent, or Firm—Paul R. Miller

[57] ABSTRACT

A thermal insulation liner is provided for a chromatograph oven. The liner is moulded as a single bucket-shaped component 1 from ceramic fibers, typically alumino-silicate, bound together with an inorganic binder. The heat capacity and thermal conductivity of this material are both very low. The inner layer of the oven can be rapidly cooled for fast throughput of analyses and there is low risk of hand burns when changing chromatograph columns. The inner surface is mouled as a smooth shape, assisting the flow of circulated air and thereby reducing hot spots. Thermal insulation for the injector and detector of the chromatograph are also mouled in together with entry holes and mounting points 3,4, 5,6 to enable an inexpensive, easily assembled oven and chromatograph to be produced.

18 Claims, 4 Drawing Sheets

U.S. Patent    Aug. 8, 1989    Sheet 3 of 4    4,854,952

CHROMATOGRAPHY APPARATUS

DESCRIPTION

This invention relates to a chromatography oven liner and to a method of manufacture thereof, to a chromatography oven and to a chromatograph.

A gas chromatograph typically comprises a chromatograph column, typically a coil of glass or quartz tubing containing a stationary phase, mounted within an oven and connected to a sample injector and to an eluent detector, which are both typically mounted on the oven. The oven is required to control the temperature of the column accurately either at a constant preset temperature or through a programme of temperature variation. Rapid air circulation within the oven is needed to maintain temperature stability, to avoid temperature gradients across the oven, and to assist in responding to temperature programmes.

Gas chromatograph ovens have typically been of a double skinned metal construction with thermal insulation provided between the skins. Such an oven is disclosed, for example, in European Patent Application No. 0131980 corresponding to U.S. Pat. No. 4,580,036. This construction has however the disadvantage of being relatively expensive to manufacture particularly if the sliding top is provided to enable easy access to the columns with a reduced risk of burns when changing columns between analyses. It should be noted that the oven temperature required for certain analyses will be such that the inner surfaces reach a temperature sufficient to cause burns to the skin of any analyst coming into contact with them unless a sufficient period is left for the oven to cool before changing the columns. This has the disadvantage of slowing the throughput of samples and increasing the time required to perform a given set of analyses. One solution to this problem which has been proposed is to provide a fresh air inlet to the oven which can be opened when the oven is to be cooled, the fan drawing in the cool air from outside the oven and circulating it within the oven to speed the cooling. However, this requires additional components which adds to the cost of manufacture.

A liquid chromatograph typically comprises a chromatograph column, a sample injector and a detector and the column may be mounted in an oven so that the column can be maintained at a desired, usually constant, temperature. Other forms of chromatograph may require an oven to maintain the column at a constant or controlled varying temperature.

It is an object of the invention to enable the provision of a chromatography oven in which one or more of the aforementioned disadvantates are mitigated.

The invention provides a chromotography oven thermal insulation liner characterised in that the liner is formed by ceramic fibres bound together with an inorganic binder moulded into a one piece component to enclose an oven cavity, the one piece component having an end wall and side walls and being open opposite the end wall.

A liner formed from this material has the advantage of having a low thermal mass and a low thermal conductivity. Such a liner is less likely to cause burns if accidentally touched by an analyst working on the columns while the oven is still hot. Consequently it becomes less important to enable easy access to the columns, for example by sliding them out from the oven, thus reducing the need for the more expensive oven construction described in EP-A No. 0131980 or for the provision of a separate fan assisted air cooling step. Further, cooling of the oven between analyses may be performed more quickly and the stabilisation of the temperature of the oven can be achieved more speedily because of the high thermal insulation and low thermal capacity of the oven liner material.

The oven liner may be produced as a single one-piece component thus reducing assembly times and costs. In this context the term moulding encompasses the technique of vacuum forming.

The inner surface of the end wall may be concave and smoothly curved and merge smoothly with the inside surfaces of the side walls, the end wall having a hole to receive the drive shaft of an air circulating fan to be mounted inside the oven, the concave surface being shaped to guide air flowing radially away from the fan and direct it along the side walls. This provides an aerodynamic shape which enhances air circulation and reduces the incidence of hot or cold spots.

Mounting points may be provided on the inner surface of the liner by moulding them integrally with the walls of the liner. This further reduces the number of separate parts required to assemble the oven giving a saving in assembly time and cost.

The liner may be arranged to house a chromatograph column, and further, apertures to allow coupling between chromatograph injectors and/or detectors and the chromatograph column may be moulded integrally with the side walls of the liner. This eliminates the need for a separate manufacturing step to provide access to the column within the oven for the connections between the sample injector and detector and the column.

The outer surface of side walls may be provided with thermally insulating projections through which the apertures pass, the projections being of the same material and being moulded integrally with the side walls.

It should be noted that the oven liner may be arranged to house a sample injector and/or a detector for a chromatograph instead of the chromatograph column. Alternatively, the liner may have a plurality of compartments, each compartment housing one of a chromatography column, a chromatography sample injector, and a chromatography detector, being substantially thermally isolated from one another, and being moulded in one piece.

The sample injector and detector ovens may be individually controlled and the connection between the sample injector and the column and/or the connection between the column and the detector may need to be kept at a constant temperature or at a given temperature gradient. It is conventional to provide a separate insulating sleeve over these connections to enable the desired temperature conditions to be maintained. By moulding the projections integrally with the liner, the insulating sleeves are provided without the need for separate components, thus reducing the assembly time and cost.

The invention further provides a method of manufacturing a gas chromatograph oven liner comprising moulding a one piece component from ceramic fibres bound together with an inorganic binder.

This enables a convenient manufacture of a gas chromatograph oven liner as a one-piece component giving a reduced manufacturing cost over conventional oven liner constructions. In this context the term moulding encompasses the technique of vacuum forming.

The invention still further provides a a gas chromatography oven including a liner as disclosed hereinbefore.

The invention yet further provides a gas chromatograph comprising a gas chromatography column mounted within an oven, a sample injector, and a detector in which the oven is as disclosed in the preceding paragraph.

Figure 2:
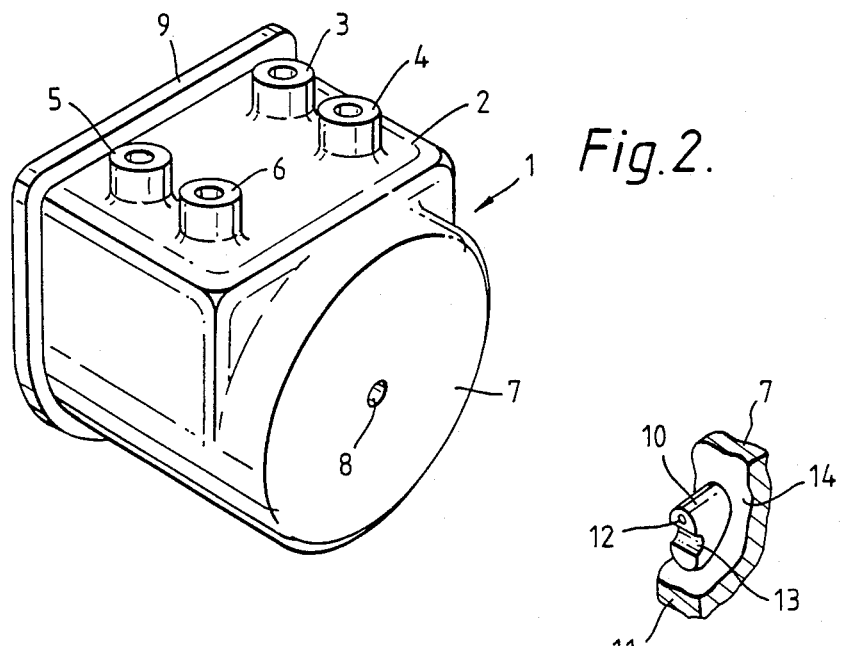
Figure 3:
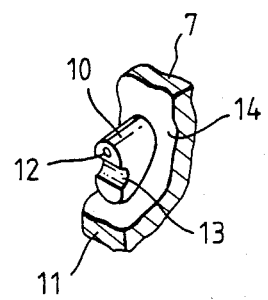
Figure 4:
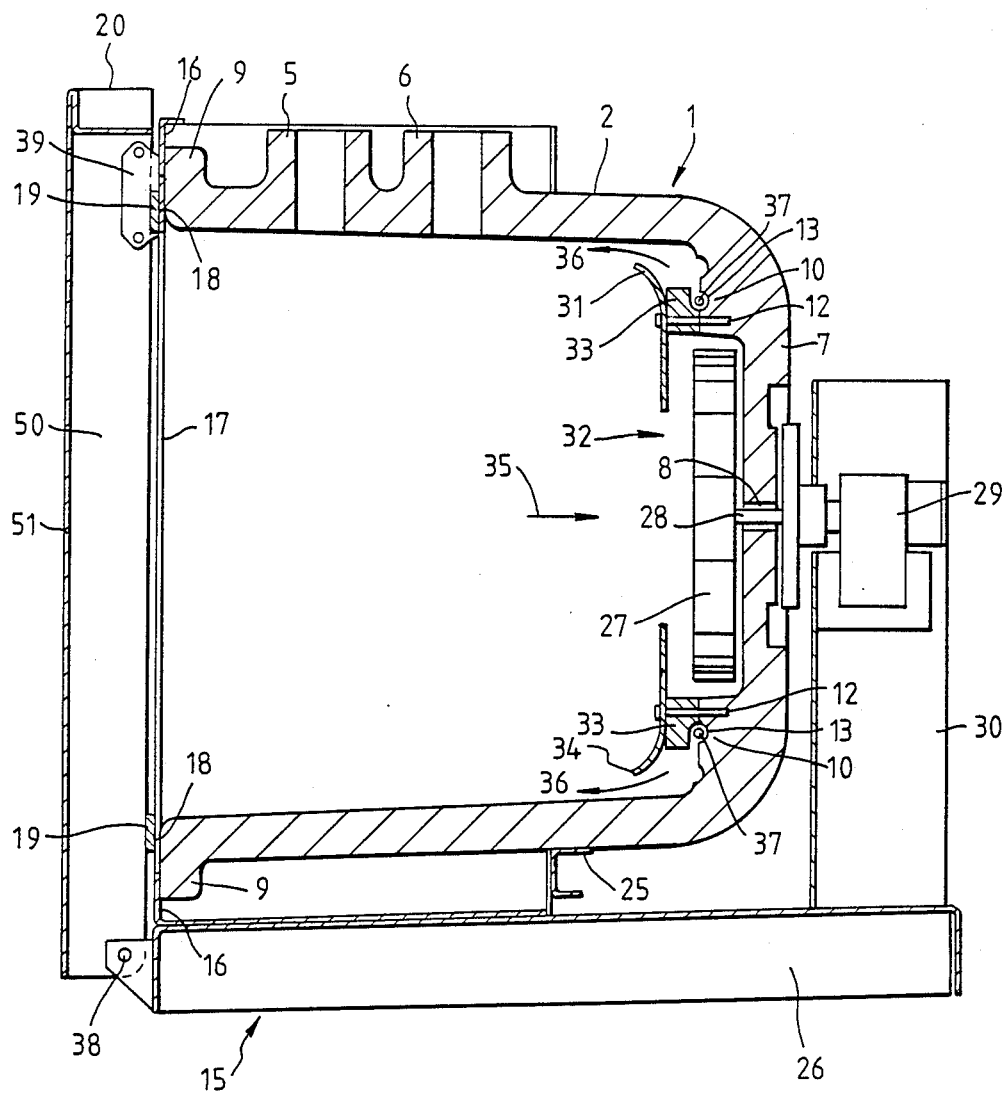
Figure 5:
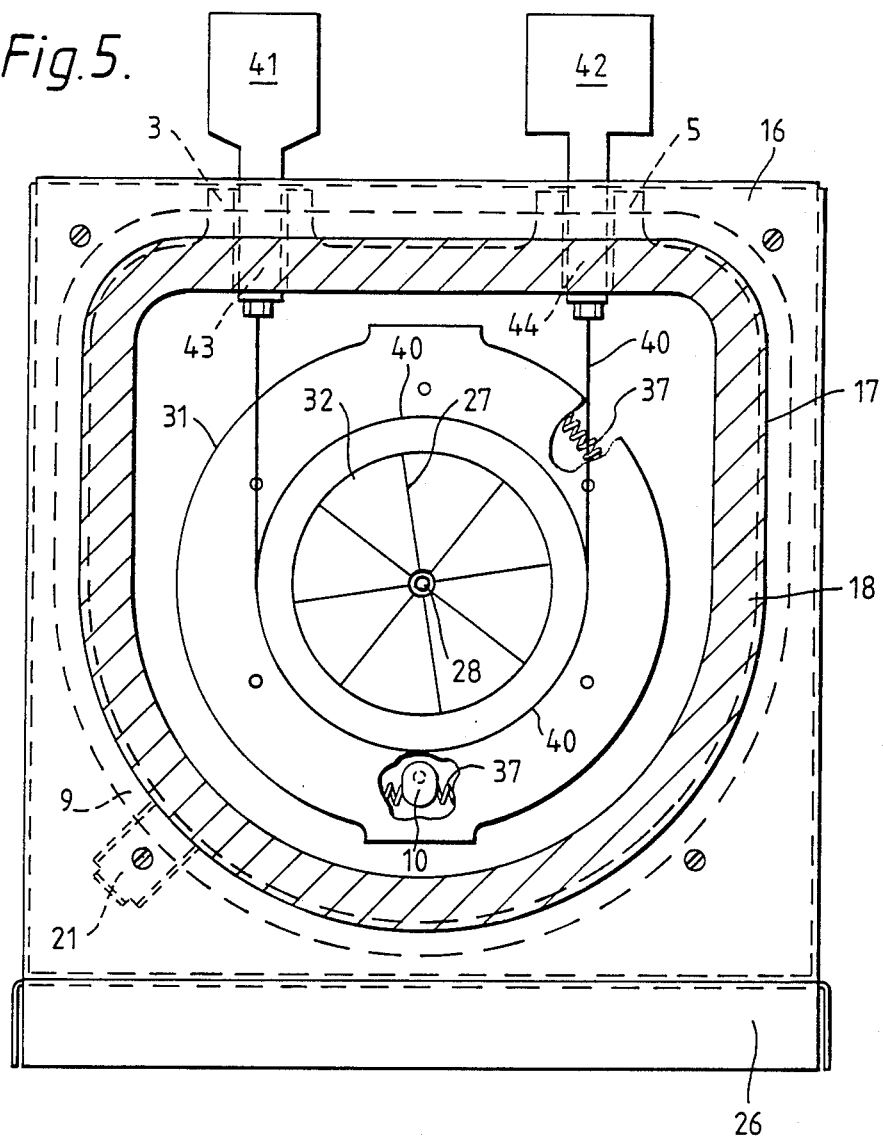
Figure 6:
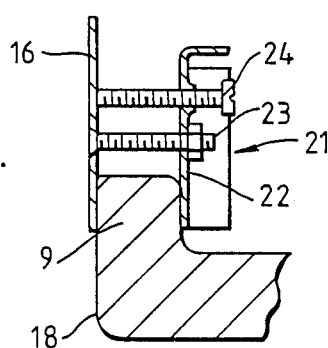
Figure 7:
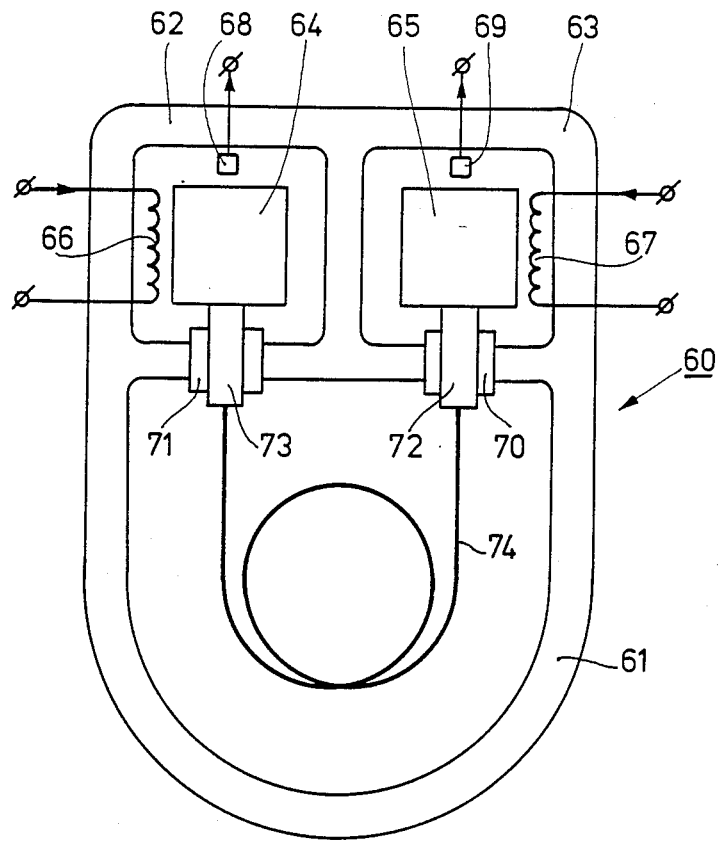

Embodiments of the invention will now be described, by way of example, with reference to the accompanying drawings in which:

FIGS. 1 and 2 show perspective views of an embodiment of a thermal insulation liner for a chromatography oven according to the invention, FIG. 3 shows a mounting point moulded onto the inside surface of the liner of FIGS. 1 and 2, FIG. 4 shows a side sectional view of a gas chromatography oven including the liner of FIGS. 1 and 2, FIG. 5 shows a front elevation view of a gas chromatograph incorporating the oven of FIG. 4, FIG. 6 shows an arrangement for clamping the liner to the front surface of the oven, and FIG. 7 shows a chromatograph with separate but integrally moulded oven liner, injector oven liner and detector oven liner.

FIGS. 1 and 2, show an oven liner 1 which is moulded from a ceramic fibre material and is arranged to accommodate a gas chromatograph column. This material is produced, typically, from alumino-silicate fibres bound together with an inorganic binder such as water glass. The process of making the liner involves chopping the fibres and forming a water slurry of them containing the inorganic binder. The slurry is poured into a mould having the desired shape and mould features and then the slurry is dewatered. Subsequent heating binds the fibres together to produce a rigid liner. Such a ceramic fibre material is available from Morgan Refractories Limited under the Trade Name Triton Kaowool, from Carborundum Resistant Materials under the Trade Name Fiberfrax, and from McKechnie Refractory Fibres Limited under the Trade Name Mackechnie ceramic fibre.

The thermal properties of this material are given below, contrasted with those of stainless steel and of water, the major constituent of human tissue. Values are taken from "Tables of Physical Constants", Kaye and Laby, 15th Edition and from manufacturers' Literature.

| SPECIFIC HEAT, Joules $g^{-1} K^{-1}$ | |
|---|---|
| Stainless steel | 0.463 |
| Water | 4.2 |
| Ceramic fibre material | 1.13 |
| THERMAL CONDUCTIVITY, Watts $m^{-1} K^{-1}$ | |
| Stainless steel | 14.5 |
| Water | 0.561 |
| Ceramic fibre material | 0.1 |
| Dense alumino-silicate | 4.5 |
| DENSITY, $g\ cm^{-3}$ | |
| Stainless steel | 7.7 |
| Water | 1.0 |
| Ceramic fibre material | 0.25 |

Thus, although the specific heat of the ceramic fibre material is more than twice that of stainless steel, its heat capacity per unit volume, 0.28 Joules $cm^3 k^{-1}$, is much less than that of stainless steel, 3.55 Joules $cm^3 K^{-1}$. The thermal conductivity of the material is less than 1% of stainless steel. Thus, having cooled the immediate surface layer of the material down by contact with human skin, little heat then reaches the surface from deeper layers. The specific heat and conductivity of the material are both considerably less than that of water. Taken with the cooling effect of blood circulation, the chance of a burn being produced by contact with the liner surface, even when hot, is much reduced. For the same reasons, the cooling of the liner surface down to a safe temperature is rapid since little heat has to be removed, only the inner surface layer being actually cooled. Rapid oven cool down is important to achieve a fast throughput of analyses.

Referring to FIGS. 1 and 2, the oven liner 1 of this embodiment forms an oven cavity of cylindrical or bucket-shape and is a one-piece component. A flat wall 2, which in use forms the upper wall, has four moulded-in insulated openings 3, 4, 5 and 6 to receive the parts of injectors or detectors which need thermal insulation, as will be described in more detail later. The end wall 7 has a central opening to receive the shaft of a fan, also to be described later. The front surface 9 of the component is formed as a flange for use in clamping the liner to a correspondingly shaped aperture in the front vertical wall of an oven.

Referring to FIG. 3, a mounting point 10 is shown moulded-in on the curved inner surface 14 of the liner joining the end wall 7 with a side wall 11. A hole 12 is provided for the attachment of parts to be described later. The cylindrical groove 13 is provided to receive a coiled resistance wire heater. The mounting points, of which there are six, take up little room on the liner inner surface. Thus, most of the curved surface 14 is free from obstructions and is concave, smoothly curved, and merges smoothly with walls 7 and 11.

Referring to FIG. 4, the liner 1 is shown fitted in a gas chromatography oven 15. The flange 9 is clamped to a front wall 16 having an opening 17 corresponding to, but larger than, the liner inner so that a free front surface 18 of the liner is available for contact by the thermal seals 19 of an oven door 20 which is hinged, 38, along its bottom edge and is held shut by a magnetic catch 39. The oven door 20 comprises a slab 50 of the same ceramic fibre material backed by a sheet metal cover 51 to present an aesthetic appearance to the outside of the oven.

FIG. 6 shows a section of one of the four clamps 21 used to couple the oven liner to the front wall 16 of the oven 15. A clamp plate 22 and screws 23 and 24 allow clamping pressure to be applied to flange 9. The rear of the liner is supported by a sheet metal structure 25 attached to the oven base 26.

A centrifugal fan 27 is mounted inside the end wall 7 of the liner on a horizontal shaft 28 of an induction motor mounted outside the liner in a sheet metal structure 30 attached to the oven base 26. A baffle plate 31 having a central aperture 32 is attached to the mounting points 10, via an insulating member 33, to assist in obtaining the desired circulation of heated air. The outer parts 34 of the baffle plate are curved to conform with the smoothly concavely curved sides of the end wall. Thus, with the fan rotating, air is drawn through aperture 32 in the direction of arrow 35 and driven radially outwards by the fan along the walls in the direction of arrows 36. Thus the flow of air is smooth, the occurrence of pockets of stagnant air which produce local hot or cold spots being minimised.

The oven is heated electrically by a resistance heater coil 37 held in position as a ring around the fan by the cylindrical grooves 13 and the insulating member 33. Thus the air flow 36 is transverse to the heater coil at all points, ensuring even heating of the air and hence of the whole oven.

FIG. 5 shows a front view of a complete gas chromatograph incorporating the oven of FIG. 4, but with the door 20 removed for clarity. A gas chromatography column 40, coiled as a multi-turn quartz tube is mounted within the liner and connected between a sample injector 41 and an eluent detector 42, both being shown only schematically since these are items well known in the art and their construction will vary according to the particular analysis to be performed. It is usual to have a variety of different sample injectors and detectors available with a given oven to enable the gas chromatography apparatus to be tailored to the particular sample analysis being carried out. The neck portions 43 and 44 of the injector and detector respectively are shown thermally insulated by the moulded-in insulated openings 3 and 5 respectively. Thus, insulation is provided for the heated and temperature controlled parts of the injector and detector by these openings which are purpose-moulded into the liner.

The oven shown in and described with reference to FIGS. 1 to 6 of the accompanying drawings is constructed for use with gas chromatographs in which one or more gas chromatography columns, which are usually formed into coils for compact construction, can be mounted. An oven for a liquid chromatography column could be constructed in substantially the same fashion but would have a different internal shape as liquid chromatography columns are normally straight rather than coiled due to their shorter length.

FIG. 7 shows a gas chromatograph 60 with separate but integrally moulded oven liner 61, injector oven liner 62 and detector oven liner 63. The injector 64 is enclosed in its oven with a heater element 66 and a temperature measuring device 68 which in use are connected in a servo loop to regulate the injector temerature to a preset value. Likewise the detector 65 has heater 67 and temperature measuring device 69 for its temperature regulation. Moulded-in inserts 70 and 71 are provided for the detector and injector lead-throughs 72 and 73 respectively, each chosen in constitution to provide a controlled temperature gradient between the column and the detector and injector. The heating arrangements for the column 74 are not shown for clarity but are similar to those shown in FIGS. 4 and 5. Thus all three ovens are integrally moulded. However, the injector and detector ovens may be moulded separately and used separately in some chromatograph constructions.

The liner, oven and chromatograph have been described above by way of example only. Variations in the size and shape of the liner and in the number and form of the mounting points and openings are entirely possible without departing from the spirit and scope of the invention.

From reading the present disclosure, other modifications will be apparent to persons skilled in the art. Such modifications may involve other features which are already known in the design, manufacture and use of chromatography systems and component parts thereof and which may be used instead of or in addition to features already described herein. Although claims have been formulated in this application to particular combinations of features, it should be understood that the scope of the disclosure of the present application also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

I claim:

1. A chromatography oven thermal insulation liner characterised in that the liner is formed by ceramic fibres bound together with an inorganic binder moulded into a one piece component to enclose an oven cavity, the one piece component having an end wall and side walls and being open opposite the end wall.

2. A liner as claimed in claim 1, in which the fibres are alumino-silicate.

3. A liner as claimed in claim 1, in which the inner surface of the end wall is concave and smoothly curved and merges smoothly with the inside surfaces of the side walls, the end wall having a hole to receive a drive shaft of an air circulating fan to be mounted inside the oven, the concave surface being shaped to guide air flowing radially away from the fan and direct it along the side walls.

4. A liner as claimed in claim 1, in which mounting points are provided on the inner surface of the liner by moulding them integrally with the walls of the liner.

5. A liner as claimed in claim 1 arranged to house a chromatograph column.

6. A liner as claimed in claim 5, in which apertures to allow coupling between a chromatograph injector and/or detector and the chromatograph column are moulded integrally with the side walls of the liner.

7. A liner as claimed in claim 6, in which the outer surface of side walls are provided with thermally insulating projections through which the apertures pass, the projections being of the same material and being moulded integrally with the side walls.

8. A liner as claimed in claim 1, in which a flange is formed on the free end on the side walls to present a flat bearing surface around the oven cavity opening.

9. A chromatography oven liner as claimed in claim 1, arranged to housed a sample injector.

10. A chromatography oven liner as claimed claim 1, arranged to house a detector.

11. A chromatography oven liner as claimed in claim 1, having a plurality of compartments each compartment housing one of a chromatography column, a chromatography sample injector and a chromatography detector, being substantially thermally isolated from one another, and being moulded in one piece.

12. A method of manufacturing a chromatography oven liner as claimed in claim 1, comprising moulding a one piece component from ceramic fibres bound together with an inorganic binder.

13. A chromatography oven characterised in that the oven comprises a liner as claimed in claim 1.

14. A chromatography oven as claimed in claim 13, having a door closing the oven cavity in which the door is lined with the same material as that from which the oven liner is formed.

15. A gas chromatograph comprising a gas chromatography column mounted within an oven as claimed in claim 13, a sample injector and a detector.

16. A gas chromatograph as claimed in claim 15 in which the sample injector and/or detector is/are mounted on the oven.

17. A gas chromatograph as claimed in claim 16, in which the connection between the sample injector and the columns and/or the connection between the detector and the column passes through apertures in thermally insulating projections moulded integrally with the side walls of the oven liner.

18. A gas chromatograph as claimed in claim 17, in which the oven liner has a plurality of compartments, each compartment housing one of the chromatography column, the sample injector and the detector, being substantially thermally isolated from one another, and being moulded in one piece.

* * * * *